United States Patent
d'Eon et al.

(10) Patent No.: US 8,538,183 B1
(45) Date of Patent: Sep. 17, 2013

(54) SYSTEM AND METHOD FOR APPROXIMATING A DIFFUSION PROFILE UTILIZING GATHERED LIGHTING INFORMATION ASSOCIATED WITH AN OCCLUDED PORTION OF AN OBJECT

(75) Inventors: Eugene J. d'Eon, San Francisco, CA (US); David Patrick Luebke, Charlottesville, VA (US)

(73) Assignee: NVIDIA Corporation, Santa Clara, CA (US)

( * ) Notice: Subject to any disclaimer, the term of this patent is extended or adjusted under 35 U.S.C. 154(b) by 1326 days.

(21) Appl. No.: 11/958,219

(22) Filed: Dec. 17, 2007

Related U.S. Application Data

(60) Provisional application No. 60/893,869, filed on Mar. 8, 2007.

(51) Int. Cl.
*G06K 9/00* (2006.01)

(52) U.S. Cl.
USPC ........... 382/252; 382/199; 382/279; 345/615; 708/420

(58) Field of Classification Search
USPC ............... 382/246, 262, 264, 108, 190, 252, 382/199; 345/611, 608, 610, 612, 615, 581; 348/325
See application file for complete search history.

(56) References Cited

U.S. PATENT DOCUMENTS

| | | | |
|---|---|---|---|
| 6,097,397 A | | 8/2000 | Lee |
| 7,231,080 B2 | | 6/2007 | Hakim et al. |
| 7,346,882 B2 | | 3/2008 | Abe |
| 7,573,474 B2 | | 8/2009 | Hoppe et al. |
| 7,679,621 B2 | * | 3/2010 | Nishiyama et al. ........... 345/611 |
| 8,064,726 B1 | * | 11/2011 | d'Eon et al. .................. 382/279 |
| 2004/0109077 A1 | * | 6/2004 | Abdellatif ...................... 348/335 |
| 2004/0193670 A1 | * | 9/2004 | Langan et al. ................ 708/819 |
| 2006/0013505 A1 | | 1/2006 | Yau et al. |
| 2006/0110052 A1 | | 5/2006 | Finlayson |
| 2006/0227137 A1 | * | 10/2006 | Weyrich et al. ............... 345/426 |
| 2007/0065015 A1 | * | 3/2007 | Nishiyama et al. ........... 382/190 |
| 2007/0223815 A1 | | 9/2007 | Makram-Ebeid |

OTHER PUBLICATIONS

Weyrich et al., "Analysis of Human Faces using a Measurement-Based Skin Reflectance Model", published in 2006 ACM.*
Wei-Yu Lee et al., "Approximation to the two-step diffusion profile by a series of Gaussian functions" Applied Physics A, vol. 46, Issue 4, pp. 281-283, Springer-Verlag 1998.*
Craig et al.,, "Light Diffusion in Multi-Layered Translucent Materials", published, Jul. 31-Aug. 4, 2005 Proceedings of ACM SIGGRAPH 2005.*
Weyrich et al.,, "A Measurement-Based Skin Reflectance Model for Face Rendering and Editing", published on Jul. 2005 by Mitsubishi Electric Research Laboratories, 13 pages.*
Weyrich et al., "Analysis of Human Faces using a Measurement-Based Skin Reflectance Model", published in 2006 AC.*

(Continued)

*Primary Examiner* — Mekonen Bekele
(74) *Attorney, Agent, or Firm* — Zilka-Kotab, PC

(57) ABSTRACT

A system and method are provided for approximating a diffusion profile utilizing gathered lighting information associated with an occluded portion of an object. In use, the present technique gathers information associated with an occluded portion of an object that is illuminated with a two-dimensional pattern of light including an edge which defines an illuminated portion and the occluded portion of the object. To this end, a diffusion profile of the object is approximated, utilizing such information.

18 Claims, 8 Drawing Sheets

(56) References Cited

OTHER PUBLICATIONS

Wei-Yu Lee et al., "Approximation to the two-step diffusion profile by a series of Gaussian functions" Applied Physics A, vol. 46, Issue 4, pp. 281-283, Springer-Verlag 1998.*

Craig et al."Light Diffusion in Multi-Layered Translucent Materials", published, Jul. 31-Aug. 4, 2005 Proceedings of ACM SIGGRAPH 2005.*

Jensen et al., "A Practical Model for Subsurface Light Transport", In Proceedings of SIGGRAPH 2001, pp. 511-518, New York, NY, USA.

Pharr et al., "Physically Based Rendering: From Theory to Implementation", Aug. 2004, Morgan Kauffman Publishers Inc., pp. 1-1065San Francisco, CA, USA.

Donner et al., "Light Diffusion in Multi-Layered Translucent Materials", Proceedings of SIGGRAPH 2005, pp. 1032-1039, vol. 24, Issue 3, Jul. 2005, New York, NY, USA.

Dachsbacher et al., "Translucent Shadow Maps", Proceedings of the 14th Eurographics Workshop on Rendering, 2003, pp. 197-201, GPU Gems: Chapter 16, Aire-la-Ville, Switzerland.

Green, Simon "Real-Time Approximations to Subsurface Scattering", Sep. 2007, pp. 263-278, NVIDIA Corporation, Pearson Education, USA.

Weyrich et al., "Analysis of Human Faces Using a Measurement-Based Skin Reflectance Model", ACM Transactions on Graphics, pp. 1013-1024, vol. 25, Issue 3, Jul. 2006, New York, NY, USA.

Wang et al., "All-Frequency Interactive Relighting of Translucent Objects with Single and Multiple Scattering", ACM Transactions on Graphics, pp. 1202-1207, vol. 24, Issue 3, Jul. 2005, New York, NY, USA.

Donner et al., "A Spectral BSSRDF for Shading Human Skin", Eurographics Association, Rendering Techniques, Jun. 2006, pp. 409-418.

Tariq et al., "Efficient Estimation of Spatially Varying Subsurface Scattering Parameters for Relighting", USC ICT Graphics Lab, Jul. 27, 2006, pp. 1-10.

Non-Final Office Action from U.S. Appl. No. 11/958,208, dated Mar. 17, 2011.

Notice of Allowance from U.S. Appl. No. 11/958,208, dated Sep. 8, 2011.

* cited by examiner

SYSTEM AND METHOD FOR APPROXIMATING A DIFFUSION PROFILE UTILIZING GATHERED LIGHTING INFORMATION ASSOCIATED WITH AN OCCLUDED PORTION OF AN OBJECT

RELATED APPLICATION(S)

The present application claims priority to a provisional application filed Mar. 8, 2007 under Application Ser. No. 60/893,869, which is incorporated herein by reference in its entirety.

FIELD OF THE INVENTION

The present invention relates to diffusion profiles, and more particularly to diffusion profiling.

BACKGROUND

Accurate rendering of many real-world objects requires modeling subsurface scattering effects to capture translucent appearance. Examples of translucent materials include, but are certainly not limited to milk, ketchup, jade, marble, plastic, etc. One important class of translucent materials, namely organic materials such as plant leaves and human skin, include multiple translucent layers. Human skin, in particular, presents a challenge for realistic rendering.

In the past, prior art systems have approximated the aforementioned subsurface scattering effects using diffusion profiles. Typically, such diffusion profiles have been captured by illuminating an object with a laser and photographing a fall off using high dynamic range (HDR) lighting techniques, etc. These systems rely on the use of expensive lasers, cameras, etc. Moreover, such laser-based systems exhibit difficulty when approximating multi-layer profiles.

There is thus a need for addressing these and/or other issues associated with the prior art.

SUMMARY

A system and method are provided for approximating a diffusion profile utilizing gathered lighting information associated with an occluded portion of an object. In use, the present technique gathers information associated with an occluded portion of an object that is illuminated with a two-dimensional pattern of light including an edge which defines an illuminated portion and the occluded portion of the object. To this end, a diffusion profile of the object is approximated, utilizing such information.

DETAILED DESCRIPTION

Figure 1:
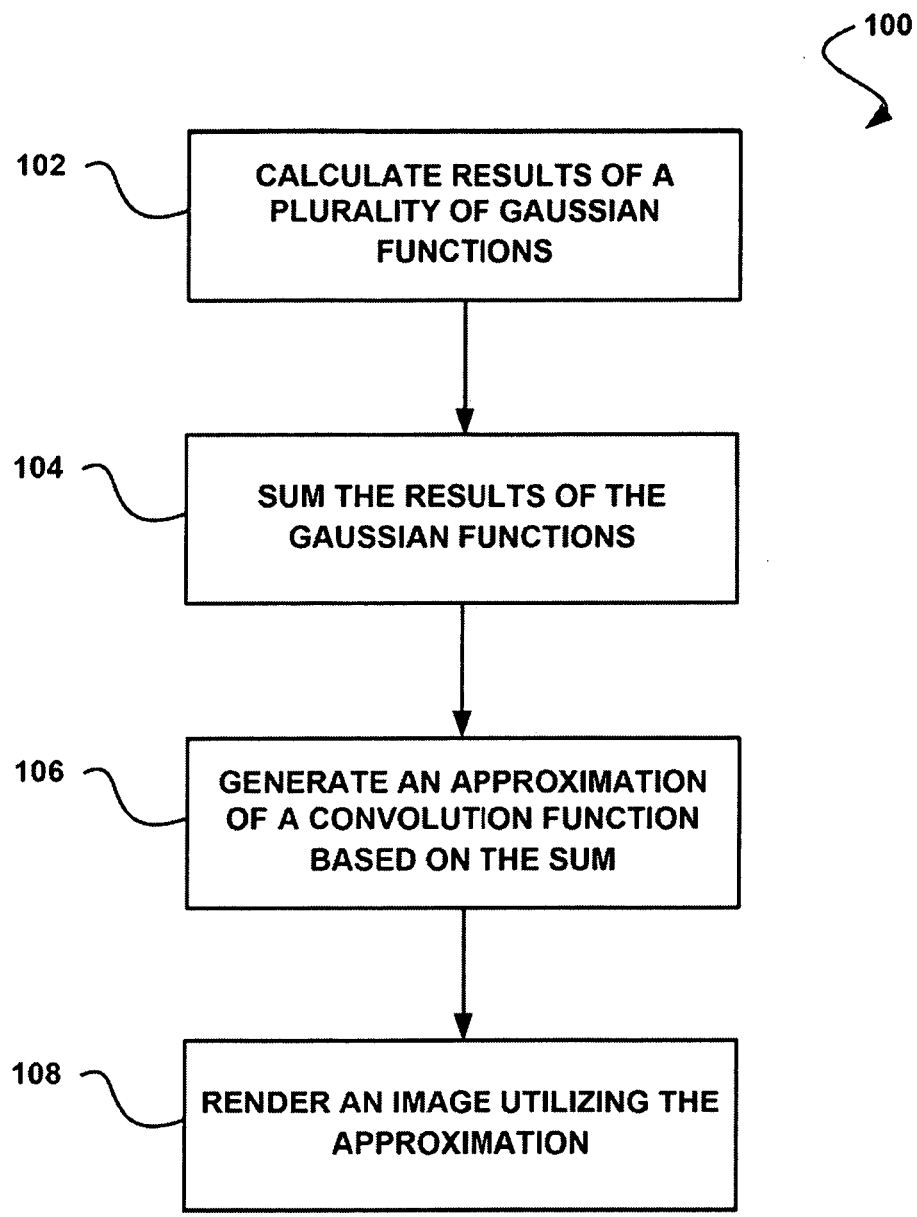
FIG. 1 shows a method for approximating a convolution function (e.g. diffusion profile, etc.), in accordance with one embodiment.

FIG. 1 shows a method 100 for approximating a convolution function, in accordance with one embodiment. In one possible embodiment, the convolution function may include a one-dimensional, non-separable, radial convolution function. In another exemplary embodiment, the convolution function may include a diffusion profile. Of course, however, the convolution function may include any convolution, in other embodiments.

In the context of the present description, the term diffusion profile may refer to any profile that describes how a wave scatters off and/or transmits through a material. For example, the diffusion profile may include, but is certainly not limited to a transmittance profile, a reflectance profile, etc. Of course, such diffusion profile may refer to any wave including, but not limited to light, heat, electromagnetic waves, neutron transport, etc.

As shown in FIG. 1, results of a plurality of Gaussian functions are first calculated. See operation 102. Such Gaussian functions may include any function that uses a Gaussian distribution. Further, the Gaussian functions may be identified in any desired manner. For example, the Gaussian functions may be identified to approximate the aforementioned convolution function. In one embodiment, the convolution function may be measured, while, in other embodiments, the convolution function may be determined from known data. Still yet, in various embodiments, the approximation may further involve weighting the Gaussian functions with corresponding weights.

The calculation of operation 102 may involve any mathematical operation. Just by way of example, in one embodiment, the results may include a plurality of convolutions of a dataset (e.g. 2D, 3D, or higher) using the Gaussian functions. In various embodiments, such dataset may be discrete, or defined analytically or implicitly. In still additional embodiments, each convolution may be separable, and can even be hierarchically built from the last, etc.

Next, in operation 104, the results of the Gaussian functions are summed. Such sum may then be used to generate an approximation of the convolution function. See operation 106. In the context of an embodiment involving the aforementioned weights, a linear combination may thus result. Therefore, in various embodiments where operation 102 involves the aforementioned convolution, the sum of Gaussian functions may be used to approximate the dataset convolved by the approximated convolution function.

By approximating the convolution function in such manner, one or more images may be rendered utilizing the approximation, thus increasing the speed with which rendering can take place. See operation 108. In some embodiments, the method 100 may be used to achieve real-time or near real-time rendering. Of course, however, embodiments are contemplated where such technique is utilized for improved offline rendering.

More illustrative information will now be set forth regarding various optional architectures and features with which the foregoing framework may or may not be implemented, per the desires of the user. Specifically, more information will be provided regarding embodiments involving convolution functions in the form of diffusion profiles. Thus, it should be strongly noted that the following information is set forth for illustrative purposes and should not be construed as limiting in any manner. Any of the following features may be optionally incorporated with or without the exclusion of other features described.

For example, in various embodiments, the aforementioned diffusion profile may be represented by dipoles and/or multipoles. In such embodiments, such dipoles and multipoles may be approximated by the sum of Gaussians of the method 100 of FIG. 1. To this end, the speed with which rendering of materials with such complex diffusion profiles may be accelerated.

In such context, it is noted that light transport in translucent materials is governed by the bidirectional scattering surface reflectance distribution function (BSSRDF). Such BSSRDF, S, gives the proportion of light incident at position $x_i$ in direction $\omega_i$ that radiates out from position $x_0$ in direction $\omega_0$. A total outgoing radiance $L_0$ is shown in Expression #1.

Expression #1

$$L_0(x_0,\omega_0) = \int_A \int_{2\pi} S(x_i,\omega_i;x_0,\omega_0) L_i(x_i,\omega_i)(\vec{n}\cdot\vec{\omega}_i) d\omega_i dA(x_i)$$

One possible dipole diffusion approximation that allows efficient simulation of highly scattering materials is shown in Expression #2.

Expression #2

$$S_d(x_i, \vec{\omega}_i : x_0, \vec{\omega}_0) = \frac{1}{\pi} F_t(x_i, \vec{\omega}_i) R(\|x_i - x_0\|_2) F_t(x_0, \vec{\omega}_0)$$

More information regarding such dipole diffusion approximation may be found with reference to JENSEN, H. W., MARSCHNER, S. R., LEVOY, M., AND HANRAHAN, P. 2001. A practical model for subsurface light transport. In Proceedings of SIGGRAPH 2001, 511-518, which is incorporated herein by reference in its entirety.

By Expression #2, S is reduced to depend only on the scattering properties of the material, the Fresnel terms at $x_0$ and $x_i$ and the distance between $x_0$ and $x_i$. It should be noted that $F_t$ is the Fresnel transmittance and R(r) is the radial diffusion profile of the material. Further information regarding such Fresnel transmittance $F_1$ may be found with reference to PHARR, M., AND HUMPHREYS, G. 2004. Physically Based Rendering: From Theory to Implementation. Morgan Kaufmann Publishers Inc., which is incorporated herein by reference in its entirety.

Using dipoles, simple analytic diffusion profiles may be derived assuming a flat, homogeneous, semi-infinite dielectric material. More information regarding multi-layered environments (without the aforementioned semi-infinite requirement) will now be set forth in the context of FIG. 2.

Figure 2:
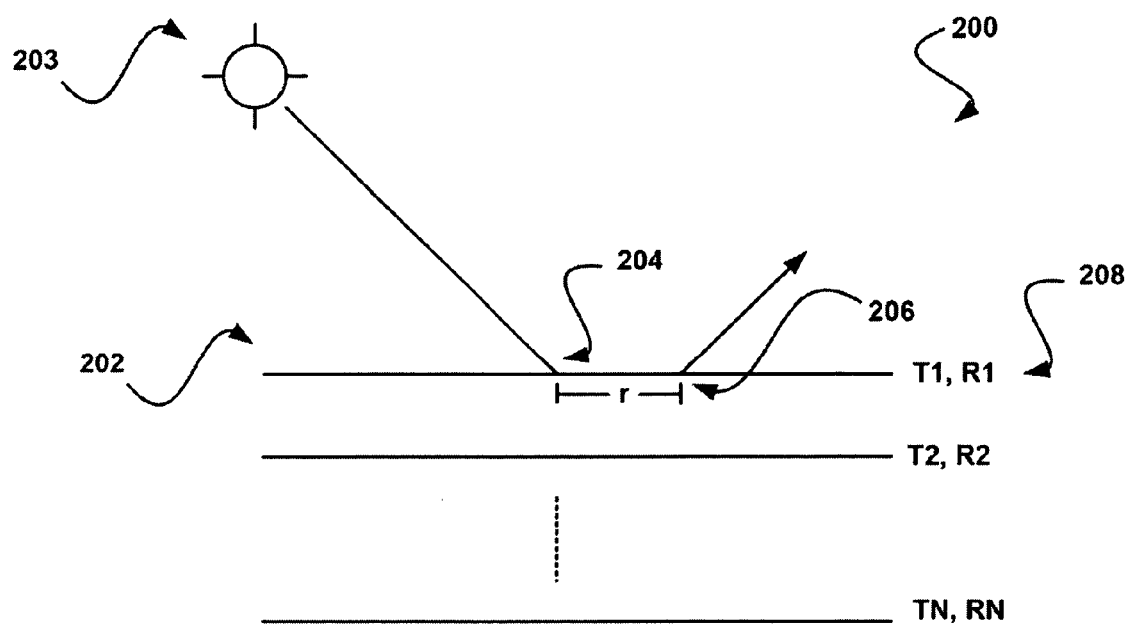
FIG. 2 shows a diagram illustrating a multi-layer environment in which a diffusion profile may be approximated, in accordance with one embodiment.

FIG. 2 shows a diagram illustrating a multi-layer environment 200 in which a diffusion profile may be approximated, in accordance with one embodiment. In one embodiment, such diffusion profile may be approximated using the method 100 of FIG. 1. While the multi-layer environment 200 is shown in FIG. 2, it should be noted that the method 100 of FIG. 1 is also applicable in single-layer environments.

As shown, a plurality of layers 202 (e.g. thin slabs, etc.) is provided which may take the form of different layers. Just by way of example, the layers 202 may represent an organic material with multiple translucent layers (e.g. plant leaves, human skin, etc.). While two (2) layers 202 are shown in FIG. 2, it should be noted that other embodiments are contemplated including any number of layers 202 [e.g. four (4), six (6), etc.]. Further shown is a light source 203 for imparting light on the layers 202.

While the light source 203 is shown to impart light on a front side of the layers 202, it should be noted that such light may also be imparted on a back side of the layers 202. This may be useful for providing additional information, for reasons that will soon become apparent.

Such light has a point of entry 204 and a point of exit 206 with a distance r therebetween. While not shown, the light is subject to a sizeable amount of scattering, reflecting, etc. amongst the various layers 202, before leaving at the point of exit 206. Such behavior is a function of a diffusion profile 208 of each of the layers 202. Each diffusion profile 208 may, in one possible embodiment, be characterized as a combination of a reflectance profile R(r) and a transmittance profile T(r), which are calculated using a multipole.

Such profiles describe how much diffuse light reflects off (or transmits through) each layer 202 due to a focused white beam of light hitting each layer 202 at the distance r from the point being considered (e.g. the point of exit 206, etc.). In one optional embodiment, different profiles may be computed for each wavelength of light being treated.

In Expression #2 discussed hereinabove, the reflectance profile R(r) may be used if $x_i$ is on the same side of the associated layer 202 as $x_0$, otherwise T(r) is used. In the case of back lighting, T(r) uses $r=\|x_0-x'_i\|$ where $x'_i$ is $x_i$ projected through the associated layer 202 to the back side in the direction of a normal of the associated layer 202. Rough surfaces may also be accounted for by modifying the Fresnel terms.

In use, the reflectance and transmittance profiles may be computed for two layers 202 placed together by analyzing the convolution of diffusion profiles of one layer 202 by that of another, as light bounces between them. More information regarding such technique may be found with reference to DONNER, C., AND JENSEN, H. W. 2005. Light diffusion in multi-layered translucent materials. In Proceedings of SIGGRAPH 2005, 1032-1039, which is incorporated herein by reference in its entirety.

Since Expressions #1-2 involve two-dimensional surface convolution of irradiance (scaled by Fresnel terms) with a radially symmetric convolution kernel R(r), associativity of convolution allows precomputation of the net kernel that describes the diffusion by the combined layers. For instance, the net diffusion profile of direct transmission through two layers without inter-layer reflection is the convolution $T_1^+(r)*T_2^+(r)$ where $T_1^+(r)$ and $T_2^+(r)$ are the forward transmittance profiles for the two layers.

Expression #3 shows an accounting for inter-layer reflections.

Expression #3

$$T_{12}^+ = T_1^+ * T_2^+ + T_1^+ * R_2^+ * R_1^- * T_2^+ + T_1^+ * R_2^+ * R_1^- * R_2^+ * R_1^- * T_2^+ \ldots$$

Here, the "+" and "−" superscripts denote reflectance and transmittance profiles in a given direction. For instance, the second term in Expression #3 accounts for light transmitting through a first layer, reflecting off a second layer, then reflecting off the first layer going backward (−), and then transmitting through the second layer going forward (+). In the case of varying indices of refraction among layers, and in the case of three or more layers, $R^+_i(r) \neq R^-_i(r)$.

To this end, each two dimensional radial profile may be transformed to frequency space where convolutions become multiplications. See Expression #4.

Expression #4

$$\mathcal{T}_{12}^+ = \mathcal{T}_1^+ \mathcal{T}_2^+ + \mathcal{T}_1^+ \mathcal{R}_2^+ \mathcal{R}_1^- \mathcal{T}_2^+ + \mathcal{T}_1^+ \mathcal{R}_2^+ \mathcal{R}_1^- \mathcal{R}_2^+ \mathcal{R}_1^- \mathcal{T}_2^+ + \ldots = \mathcal{T}_1^+ \mathcal{T}_2^+ (1 + (\mathcal{R}_2^+ \mathcal{R}_1^-) + (\mathcal{R}_2^+ \mathcal{R}_1^-)^2 + (\mathcal{R}_2^+ \mathcal{R}_1^-)^3 \ldots)$$

It can further be noted that the geometric series can be replaced, provided $\mathcal{R}^+_2(r)\mathcal{R}^-_1 < 1$ for all r, leaving that shown in Expression #5.

Expression #5

$$\mathcal{T}_2^+ = \frac{\mathcal{T}_1^+ \mathcal{T}_2^+}{1 - (\mathcal{R}_2^+ \mathcal{R}_1^-)}$$

Note that similar derivations apply for $\mathcal{T}^-_{12}(r)$, $\mathcal{R}^+_{12}(r)$, and $\mathcal{R}^-_{12}(r)$.

Again, more information regarding such technique may be found with reference to DONNER, C., AND JENSEN, H. W. 2005. Light diffusion in multi-layered translucent materials. In Proceedings of SIGGRAPH 2005, 1032-1039, which is incorporated herein by reference in its entirety.

To this end, a combination of any number of layers is permitted (plus an optional semi-infinite bottom layer), treating two at a time. Given material properties of two layers, eight radial profiles ($T_{1,2}^{+,-}(r), R_{1,2}^{+,-}(r)$) are computed using the multipoles. Eight (8) Fast Fourier transforms (FFTs) [and/or eight (8) 1D Hankel transforms] transform the profiles (applied radially in two dimensions) to frequency space, and then four formulae ($\mathcal{R}_{12}, \mathcal{T}_{12}^{+,-}(r)$) are applied to compute four frequency-space profiles of the combined layers. This may be repeated recursively for additional layers, treating the current collection of k layers as layer 1 and adding layer k+1 as layer 2. Finally, two inverse FFTs produce the reflectance and transmittance profiles used for rendering.

As mentioned previously, dipoles and multipoles that represent diffusion profiles may be approximated with sums of a number of Gaussians. In various embodiments, four Gaussians may be found to fit most single layer profiles, and more can be used to increase accuracy. To fit Gaussians to a diffusion profile R(r), one may minimize Expression #6 below.

Expression #6

$$\int_0^\infty r \left( R(r) - \sum_{i=1}^k w_i G(v_i, r) \right)^2 dr$$

Both the weights $w_i$ and the variances $v_i$ for k Gaussians may vary. In addition, error terms are weighted by r as profiles are applied radially, each value combining light from a circle of circumference proportional to r. The Gaussian of variance v is described in Expression #7 below.

Expression #7

$$G(v, r) := \frac{1}{2\pi v} e^{-r^2/2v}.$$

Figure 3:
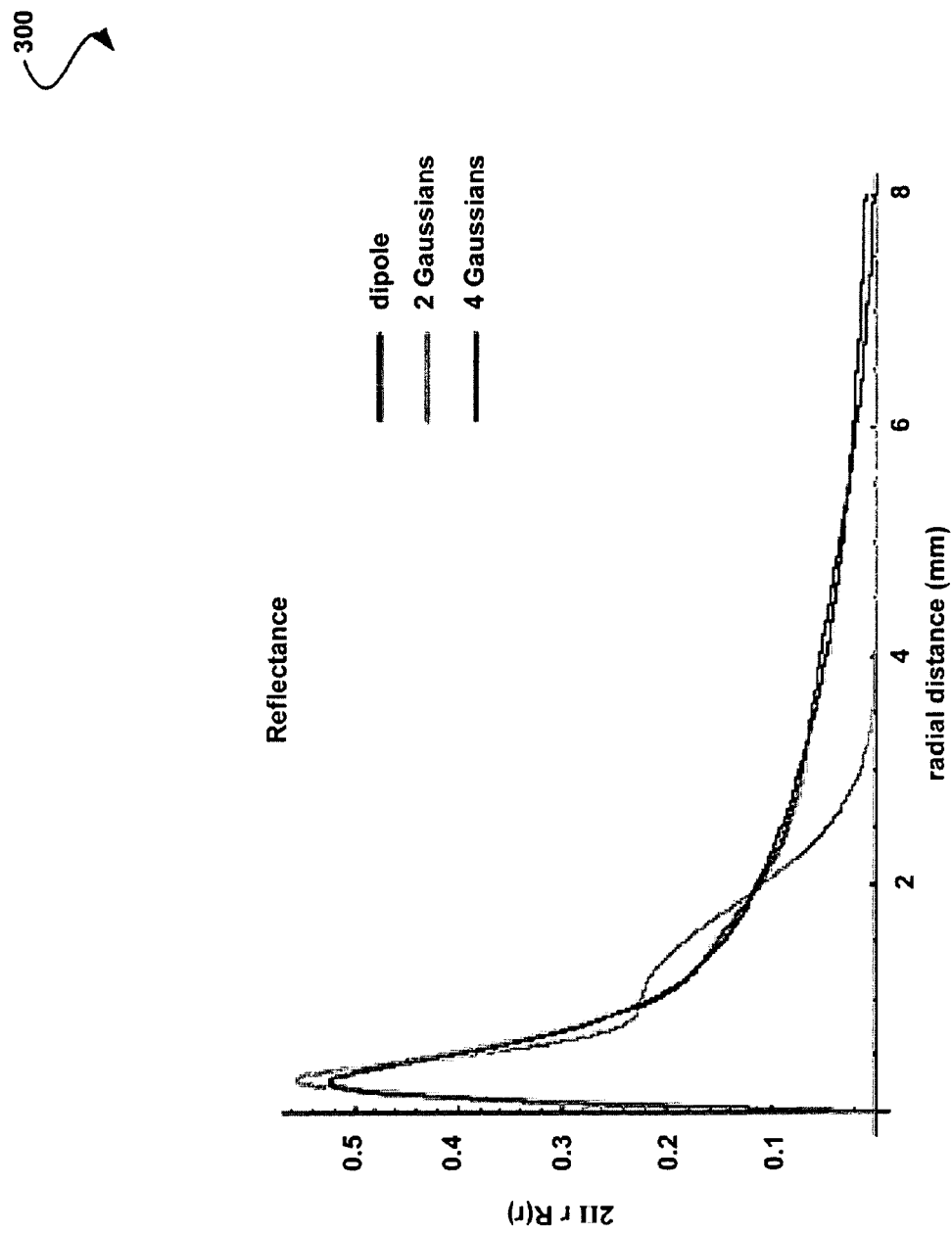
FIG. 3 shows the approximation of a dipole with a sum of 2 and 4 Gaussians, in accordance with one embodiment.

FIG. 3 shows an approximation 300 of a dipole with a sum of 2 and 4 Gaussians, in accordance with one embodiment.

Sums of Gaussians may be used in the context of the present embodiment for a variety of reasons. First, since Gaussians are separable, they can be applied as two one-dimensional convolutions in x and then y over a surface. This allows a fast estimate of the surface irradiance convolution, shown in Expression #1, provided the surface is roughly planar (which is already assumed in the derivation of the dipole and multipole theories). The convolution by the non-separable kernel R(r) may be estimated as the sum of convolutions by each separable Gaussian term. Second, convolution by a wider Gaussian can be computed from the result of a previous convolution by a narrower Gaussian, considerably faster than from the original irradiance values.

Once a dipole or multipole profile is given as a sum of Gaussians, the convolutions to combine two layers (see Expression #3) become less expensive, not necessarily requiring Fourier transforms, etc. The radial two-dimensional convolution of any two Gaussians is another Gaussian as shown in Expression #8.

Expression #8

$$G(v_1) * G(v_2) = G(v_1 + v_2)$$

The two-dimensional convolution of two radial profiles, each of which is approximated as a sum of Gaussians, is shown in Expression #9.

Expression #9

$$\sum_{i=1}^{k_1} w_i G(v_i, r) * \sum_{j=1}^{k_2} w'_j G(v'_j, r) = \sum_{i=1}^{k_1} \sum_{j=1}^{k_2} w_i w'_j G(v_i, r) * G(v'_j, r)$$

The result is a set of $k_1 k_2$ Gaussians. In some embodiments, this may or may not avoid the FFTs and inverse FFTs required to combine two layer profiles. Although Expression #3 contains an infinite number of convolutions and additions, the summation of powers of $R_2^+ R_1^-$, in practice, can be terminated more quickly with negligible error. Computing the total diffuse response $$\left( \int_0^\infty 2\pi r R(r) d(r) \right)$$

of each profile input to Expression #3, and using Expression #5, provides an accurate estimate of the total diffuse response of the geometric series of convolutions in Expression #3. This, in turn, provides a useful error metric for terminating the infinite series using the Gaussian convolution method. Comparing the current estimated total diffuse response to the known target, each Gaussian has a total diffuse response of 1.

In one embodiment, tracking the total diffuse response of the summation and comparing to the value predicted by Expression #5 may allow for early termination of the summation of powers. For example, when computing the profile for combined transmission by two slabs (e.g. Expression #3), n may be found as described in Expression #10 below.

Expression #10

$$\frac{T_{1d}^+ T_{2d}^+}{1 - (R_{2d}^+ R_{1d}^-)} - T_{1d}^+ T_{2d}^+ \left( \sum_{i=0}^{n} (R_{2d}^+ R_{1d}^-)^i \right) < \varepsilon$$

In Expression #10, the d subscript refers to the total diffuse response of each profile, and $\in$ is the maximum tolerated energy loss in terminating the infinite series of inter-slab reflections at n. The total diffuse response of any profile represented as a sum of Gaussians is simply the sum of the weights. Expression #10 uses the quickly computed total known diffuse response and compares the current sum of the inter-slab reflections to a known total until the current sum of the inter-slab reflections and the total sum are close.

Expression #9 squares the number of Gaussian terms after each multiply, causing the number of operations to accumulate quickly. However, fitting all initial layer profiles to powers of a smallest narrow Gaussian of variance v, causes any two Gaussians to convolve back into the same set. That is, each R(r) and T(r) profile is approximated as a linear combination of $\{G(v), G(v)*G(v), G(v)*G(v)*G(v), \ldots\}$, which by Expression #8 is equivalent to $\{G(v), G(2v), G(3v), \ldots\}$.

It should be noted that convolutions and additions of scattering profiles may be analogous to polynomial multiplications and additions over Gaussians. Thus, a lengthy process involving two-dimensional array additions, multiplications, divisions and FFTs may be reduced to no more than a small number of polynomial operations.

In one embodiment, the Levenberg-Marquardt optimization may be used to solve Expression #6. In another embodiment, closed formulae may be used that empirically give a close fit to any dipole over a wide range of material parameters, using 8 Gaussians. More information regarding such an optional technique will now be set forth. It should be strongly noted, however, that the following details are set forth for illustrative purposes only and should not be construed as limiting in any manner whatsoever.

A pattern may be observed as to the way four Gaussians optimize to fit a given pole equation, which allows fast analytic fitting of four Gaussians to any pole equation with no Levenberg-Marquardt minimization code or convergence concerns, in some embodiments. The profiles for dipoles and multipoles depend on r in the manner described in Expression #11 below.

Expression #11

$$P(r, \sigma_{tr}, z) = \frac{(1 + \sqrt{z^2 + r^2}\, \sigma_{tr}) e^{-\sqrt{z^2 + r^2}\, \sigma_{tr}}}{(z^2 + r^2)^{\frac{3}{2}}}$$

Expression #11 satisfies $$P_d(\sigma_{tr}, z) = \int_0^\infty P(r, \sigma_{tr}, z) r\, dr = e^{-\sigma_{tr}|z|}/|z|.$$

Finding a single Gaussian with equal power and equal x-intercept gives $w_0 G(v_0, r)$, with $w_0(\sigma_{tr}, z) = 2\pi P_d(\sigma_{tr}, z)$ and $v_0 = P_d(\sigma_{tr}, z)/P(0, \sigma_{tr}, z)$. This provides an analytic single Gaussian fit to any pole, however it is not necessarily sufficiently accurate for rendering in some embodiments. Further analysis of fitting has revealed the spread of Gaussian variances to be invariably close to $\{0.2304v_0, 0.7225v_0, 2.6569v_0, 13.6v_0\}$ for a wide range of $\sigma_{tr}$ and z. With these variances, the four weights are $w_i = C_i(|\sigma_{tr}Z|)P_d(\sigma_{tr}, z)$, where $C_i$ are four curves which have fairly simple analytic approximations (see Expression #12). Fitting each pole independently with 4 Gaussians, 8 Gaussians may be found that fit any dipole with minimal error.

Expression #12

$$C_1(x) = -0.3454 + \frac{1.2422}{x} - 1.2422\frac{e^{-0.7452x}}{x}$$

$$C_2(x) = 5.34071 \left( \frac{(1 - e^{-0.716x})(0.9029x - 0.7401)}{x} + 0.90295 e^{-0.7165x} \right)$$

$$C_3(x) = 10.2416 \left( \frac{(1 - e^{-1.096x})(0.2420x + 0.1804)}{x} - \right.$$

$$\left. 0.00244 e^{-1.0961x}(0.2041x + 0.1752) \right)$$

$$C_4(x) = 23.185 \left( \frac{(1 - e^{-1.433x})(0.0505 - 0.0395x)}{x} + \right.$$

$$\left. 0.04425 e^{-1.433x}(0.09187x + 0.06034) \right).$$

In one embodiment, the sum-of-Gaussians approximation scheme, described in detail above, may be used for diffuse scattering profiles to enable real-time rendering of multi-layer translucent materials under dynamic all-frequency lighting. Extensions to the texture-space diffusion and translucent shadow map algorithms are described in further detail below in the context of FIG. 4. It should be noted that such extensions may potentially allow one to avoid precomputation and thus render arbitrary deformable meshes, when desired.

Figure 4:
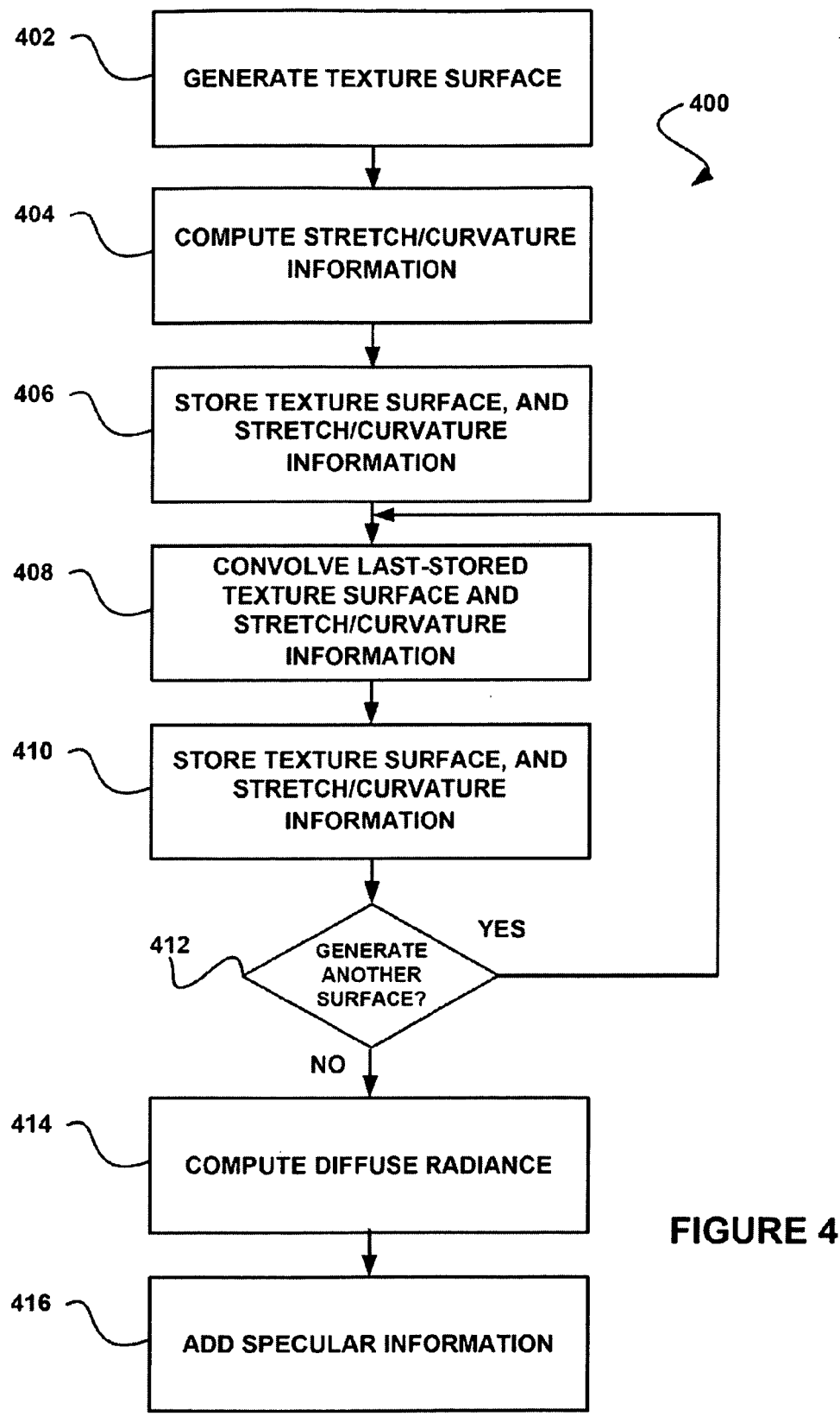
FIG. 4 shows a method for rendering an image, in accordance with another embodiment.

FIG. 4 shows a method 400 for rendering an image, in accordance with one embodiment. In one embodiment, such method 400 may take advantage of the approximation of a diffusion profile, as set forth in the context of the previous figures. Of course, such method may be employed in the context of any environment.

As shown in operation 402, a texture surface is generated including both color and depth information (e.g. R, G, B, depth values, etc.). Such information may, in one embodiment, be stored in an off-screen buffer. In another embodiment, a parameterized mesh may be used (e.g. a 1:1 UV parameterization, or a series of charts plus a partition of unity, etc.). Further, an irradiance function (attenuated by $\rho_{dt}$) may be convolved over the mesh by rasterizing irradiance into an off-screen texture in the aforementioned off-screen buffer.

After or in parallel with operation 402, both stretch and curvature information may be computed. Note operation 404. In one embodiment, such stretch and curvature information may be dynamically generated utilizing fragment shaders or any desired mechanism, for that matter. Further, in one embodiment, a stretch value and curvature value may be stored for each u and v value associated with the texture surface of operation 402. For reasons that will soon become apparent, the color, depth, stretch, and color information of operations 402-404 may be stored for later use. Note operation 406.

In possible embodiments, various graphics processor derivative instructions of a fragment shader may be used to quickly estimate the aforementioned stretch value. Further, various techniques may be used to efficiently compute normal curvature over a general mesh (with or without displacement, bump, or normal maps, etc.).

Next, in operation 408, a previously-stored texture surface and the associated stretch/curvature information may be convolved to provide a new blurred texture surface. In one optional embodiment, the texture space stretching and normal curvature may be convolved simultaneously with irradiance (e.g. in a separate 4 channel texture, etc.). As will soon become apparent, the convolution of stretch/curvature information is what prevents small scale features from affecting large scale convolution. Again, the results of such convolution may be stored as set forth in operation 410.

Both the stretching and normal curvature modulate each separable blur convolution step, providing a more accurate accumulation of samples based on the true distance between them in space. The stretch information may directly scale the spread of the separable samples in texture space. Further, surface curvature may be used to modulate the shape of the (otherwise) Gaussian kernels using a simple heuristic.

As the effective radius, roughly 3v, of the current convolution step approaches π times the radius of normal curvature 1/K, all samples along the surface are then equidistant from a virtual source a distance 3 v/π below the surface. Therefore, one approach may involve blending towards a unit power box filter as 3vapproaches π/K. If, however, the mean free path is not comparable to 3v, the current convolution step may not necessarily be heavily weighted in approximating the material profile. This change may be lost in further convolution steps, thereby eliminating the introduction of unwanted error.

Thus, a basis set of Gaussian convolutions for a current texture is computed, taking into account normal curvature and texture space stretching in each direction. For efficiency, such convolution may comprise a two step process involving a first multi-point vertical tap followed by a second multi-point horizontal tap (e.g. the convolution may be performed separately in u and v, etc.), and convolution kernels may be chosen such that each convolution step operates hierarchically on the result of the previous step (as will soon become apparent), etc.

As indicated in decision 412, operations 408-410 may be repeated as desired to generate multiple instances of the texture surface and the associated stretch/curvature information. The number of convolutions and resulting texture/stretch/curvature information may, in some embodiments, be equal to the number of Gaussians that can eventually be used to approximate the diffusion profile.

Thereafter, a diffusion radiance may be computed in operation 414. To this end, the information may be weighted and combined. Thus, a complete basis of radial Gaussian convolutions may be combined in a final render pass using texture mapping. In various embodiments, the basis functions may be combined separately in R, G, and B to accurately match the diffusion profiles of the material, and the total diffuse exitance may be scaled by $\rho_{dt}$ and combined with specular reflection. See operation 416.

During the final render pass, an average depth may be computed through the surface (from the point of the light) from the basis of convolved distances (as will be elaborated upon later in greater detail). Appropriate convolutions of irradiance may then found at the point of entry by sampling the convolved irradiance textures at the coordinates (u,v) stored in the translucent shadow map. The local and global scattering terms may further be combined based on the proximity of the coordinates (u,v) where light enters and the coordinates (u,v) of the point being rendered (favoring the local scattering approximation and scaling away the global scattering contribution as the two locations in texture space approach each other).

In various optional embodiments, translucent shadow maps may be modified to account for forward scattering through thin regions. It should be noted that, whereas translucent shadow maps render the depth, irradiance, and surface normal, and thus store these quantities for the surface nearest the light (the "light facing surface") at every pixel of the shadow map, the present embodiment renders and stores the coordinates (u,v) along with depth. More information regarding translucent shadow maps may be found with reference to DACHSBACHER, C., AND STAMMINGER, M. 2003. Translucent shadow maps. In Eurographics Symposium on Rendering: 14$^{th}$ Eurographics Workshop on Rendering, 197-201, which is incorporated herein by reference in its entirety.

Still yet, in additional embodiments, the depth may be estimated through the surface from the topmost surface from the point of view of light. More information regarding such technique may be found with reference to GREEN, S. 2004. Real-time approximations to subsurface scattering. In GPU Gems, R. Fernando, Ed. Addison Wesley, Mar., ch. 16, 263-278, which is incorporated herein by reference in its entirety.

Furthermore, a set of multiscale depth convolutions may be built along with irradiance (e.g. depth through the surface may be stored in the alpha channel of the convolved textures, etc.). In the original translucent shadow map algorithm, high frequency changes in depth through the surface can cause unwanted high frequency artifacts, which may be reduced by using a better estimate of average depth.

In one embodiment, the (u,v) coordinates and depth of the light facing surface are rendered and stored to allow every shadowed surface location to compute distance through the object toward the light, and to access convolved versions of irradiance on the light facing surface by looking up into the same irradiance textures used for local scattering. For example, at any shadowed location (e.g. point C), the translucent shadow map provides a distance or depth (m) and the (u,v) coordinates of a point on the light-facing surface (e.g. point A).

It may be desirable to estimate the scattered light exiting at the shadowed location C, which is the convolution of irradiance at each light-facing point by a profile (R) through the thickness of an object. The convolution may instead be computed at a point B which is directly in line with point A (i.e. a 90 degree angle between the light facing surface, point A, and point B), since this computation may be accomplished very efficiently. It should be noted that, for low angles (0), B may be close to C, and for high angles, the Fresnel term may reduce the contribution. The convolution kernel is shown in Expression #13 below.

Expression #13

$$R\left(\sqrt{r^2+d^2}\right) = \sum_{i=1}^{k} w_i G\left(v_i, \sqrt{r^2+d^2}\right) = \sum_{i=1}^{k} w_i e^{-d^2/v_i} G(v_i, r)$$

In this example, d=m cos(θ) may represent the thickness of the object. Because the Gaussians are separable in the third dimension, global transmittance is the weighted sum of k texture lookups, each weighted by $w_i e^{-d^2/v_i}$, where i is the index corresponding to the irradiance texture convolved by $G(v_i, r)$. In the current example, a single 2D convolution of irradiance on the light facing surface with R(r) may not be re-used to compute transmittance in this fashion because R is not a separable kernel. However, by expressing R(r) as a sum of Gaussians, the convolution textures may be used for both local scattering at point A and global transmittance at point B. Thus, the weighted sums may accurately match the convolution by the original profile.

In the current example, the depth (m), computed by the shadow map, is corrected by cos(θ), since a diffusion approximation is being used and the most direct thickness may be more applicable. Surface normals at point A and point C may be compared and the distance correction applied when the surfaces are oppositely facing. As an example, an interpolation between the points may be accomplished using: lerp (m,m cos(θ),max(0,$-N_A \cdot N_C$)).

It should be noted that the derivation described in the current example assumes a planar surface with constant thickness d. This is similar to the dipole and multipole theories, which were derived in a plane-parallel setting but are directly applied to curved surfaces. Of course, this assumption may not hold for 3D models in general, however directly applying the technique to curved surfaces may be desirable.

In one embodiment, the depth (m) may be convolved through the surface, over the surface of the object. For example, $e^{-m*k}$ may be convolved over the surface over the surface of the object, where k is a constant. Although, this embodiment is described in the context of the current example, such embodiment may be implemented in the context of other various embodiments and examples.

Further, high-frequency changes in depth through the surface may create high-frequency artifacts in a final image. In one embodiment, the depth may be convolved simultaneously with irradiance by storing the depth in an alpha channel before convolving the irradiance textures, to mitigate these effects. Computation of forward transmittance for each Gaussian i then may use the convolved depth from irradiance texture i−1.

To avoid double contribution from both local and global scattering, the global scattering terms may be interpolated to 0 as the (u,v) coordinate of the point being rendered (e.g. point C) approaches the (u,v) coordinate of the light facing surface at a point (e.g. point A). In one embodiment, a separate interpolation may be used for each Gaussian starting when the two locations are a distance $6\sqrt{v_i}$ apart.

Additionally, in one embodiment, the diffuse color map may be treated as an infinitesimal, highly absorptive layer that absorbs light once as it enters the surface and once as it leaves. More information regarding such technique may be found with reference to WEYRICH, T., MATUSIK, W., PFISTER, H., BICKEL, B., DONNER, C., TU, C., MCANDLESS, J., LEE, J., NGAN, A., JENSEN, H. W., AND GROSS, M. 2006. Analysis of human faces using a measurement-based skin reflectance model. ACM Transactions on Graphics 25, 3 (July), 1013-1024, which is incorporated herein by reference in its entirety.

It should be noted that the application of the sum-of-Gaussians approximation scheme, described in detail above, is not limited to enabling real-time rendering of multi-layer translucent materials under dynamic all-frequency lighting. For example, other embodiments may include, but are not limited to the sum-of-Gaussians approximation scheme being used for diffuse scattering profiles to enable efficient offline rendering of multi-layer translucent materials under dynamic all-frequency lighting. In addition, such sum-of-Gaussians approximation scheme may be applied to rendering of single-layer translucent materials under dynamic all-frequency lighting.

An exemplary implementation of the method 400 of FIG. 4 is set forth in Table #1 below.

TABLE #1

Render irradiance texture:
    Render Translucent Shadow Map (TSM)
    Render any other shadow maps
    Irrad = sum of diffuse light from point, spot,
    environment lights
    Irrad *= Fresnel term rdt (xi)
    Irrad *= sqrt(diffuse color)
    Irrad.alpha = distance through surface, from the TSM
Render Stretch-and-Curvature texture:
    Simple fragment program with derivative instructions
    Stretch = four channel texture of U stretch, V stretch,
    U curvature, and V curvature
// Gaussian basis is G(v), G(2v), ..., G(kv)
For i = 1 to k, compute Irrad convolved by G(i*v):
    Blur Stretch by v in U direction, compensated by
    Stretch
    Blur Irrad by v in U direction, compensated by Stretch
    Blur Stretch by v in V direction, compensated by
    Stretch
    Blur Irrad by v in V direction, compensated by Stretch
    // Now Stretch and Irrad are blurred by i*v in both U
    and V
    IrradBasis[i] = Irrad
Render final image:
    Render mesh in 3D, reading from textures
    Image = 0
    For i = 1 to k :
    Image += wi * IrradBasis[i]
    AvgDist = average distance through surface based on
    IrradBasis[i].alpha
    w0i = weight of global scattering based on AvgDist
    and TSM
    Image + = w0i * IrradBasis[i] at the (u,v) from the TSM
    Image *= Fresnel term rdt (xo)
    Image *= sqrt(diffuse color)
    Image += sum of specular term of lights Of course, such exemplary implementation is set forth for illustrative purposes only and should not be construed as limiting in any manner whatsoever.

In another embodiment, a simple image-based technique may be used to capture approximate reflectance and transmittance profiles for multi-layered materials. Such embodiment may be particularly useful where various information (e.g. scattering properties, thickness, etc. of various layers, etc.) of a multi-layer object is not known. More information regarding such embodiment will now be set forth in the context of FIG. 5.

Figure 5:
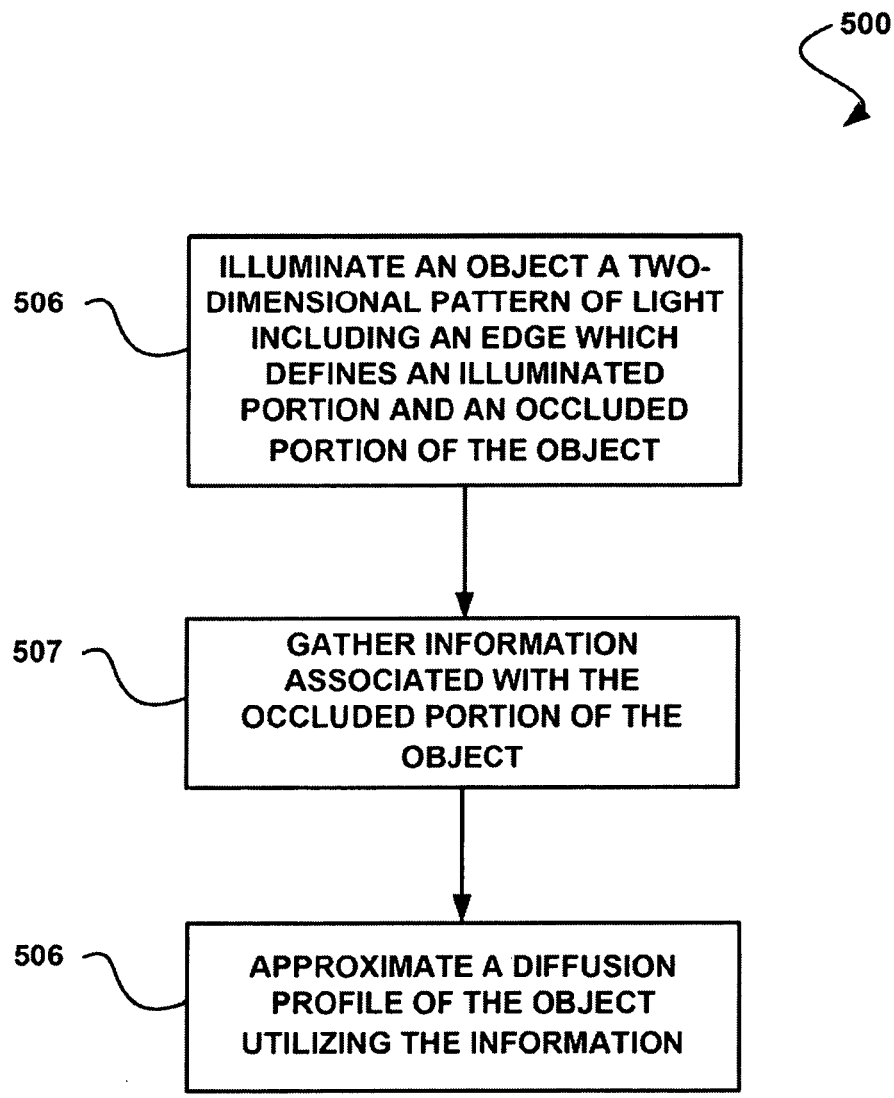
FIG. 5 shows a method for approximating a diffusion profile utilizing gathered lighting information associated with an occluded portion of an object, in accordance with one embodiment.

FIG. 5 shows a method 500 for approximating a diffusion profile utilizing gathered lighting information associated with an occluded portion of an object, in accordance with one embodiment. In one embodiment, such method 500 may take advantage of the approximation of a diffusion profile, as set forth in the context of the description of the previous figures. Of course, such method 500 may be employed in the context of any environment.

As shown, an object is illuminated with a two-dimensional pattern of light. See operation 502. In the context of the present description, such object may include absolutely anything capable of having a diffusion profile. In one optional embodiment, the object may include a plurality of layers in the form of a multi-layer object.

Further, the pattern of light includes an edge which defines an illuminated portion and an occluded portion of the object. In one embodiment, the two-dimensional pattern may be provided utilizing an occluder that is positioned closer to the object than the light source, and occludes light from illuminating part of the object. Such occluder may, in turn, include a white diffuse object, in some embodiments. As an option, the two-dimensional pattern may change as a function of time. More illustrative information regarding one possible way the object may be illuminated will be set forth during the description of FIG. 6.

With such illumination, information associated with the occluded portion of the object may be gathered (with or without information associated with the illuminated portion of the object). Note operation 504. In the context of the present description, such information may include any data associated with the occluded portion of the object that may be used in approximating a diffusion profile of the object, as will soon become apparent. In one embodiment, the information may describe light scattered from the illuminated portion of the object. In various embodiments, such information may be gathered utilizing a camera. In some embodiments, operation 502 may be omitted in a situation where the foregoing information is gathered directly from a pre-captured image, etc.

To this end, a diffusion profile of the object may be approximated utilizing the information gathered in operation 504. See operation 506. In one embodiment where the aforementioned occluded/illuminated edge at least substantially represents a step function, and the information gathered in operation 504 describes light scattered from the illuminated portion of the object; such information may be considered to represent an integral, or "pre-integration," of the step function, which may, in turn, be exploited in any one of a number of ways to approximate the diffusion profile. More illustrative information regarding various possible techniques for approximating the diffusion profile will be set forth in greater detail during the description of subsequent figures.

Figure 6:
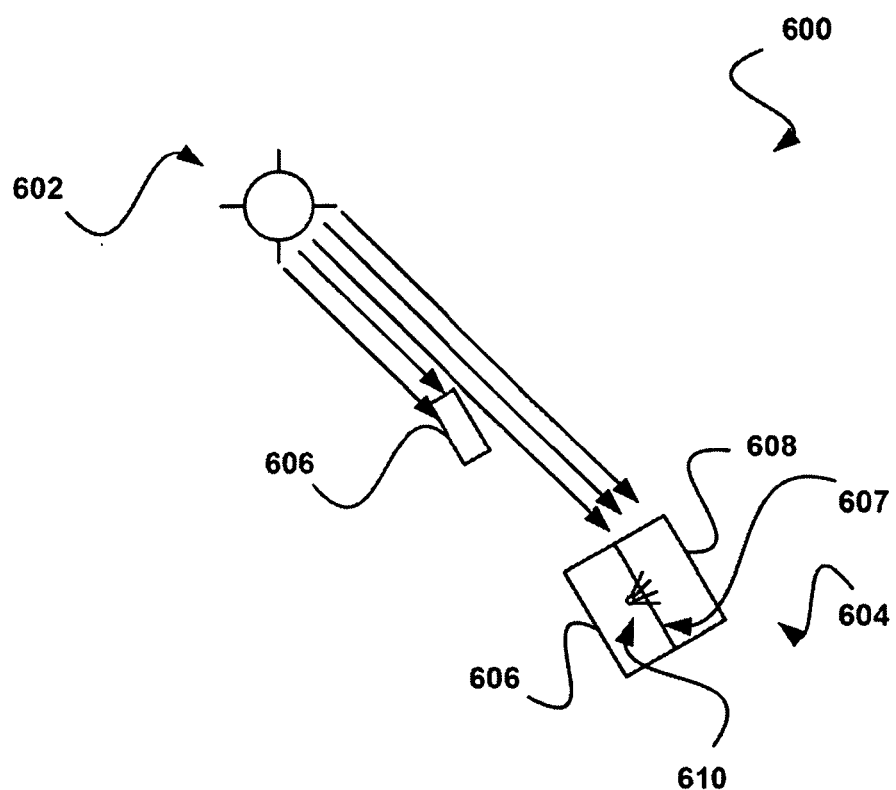
FIG. 6 shows a system for illuminating an object for the purpose of approximating a diffusion profile, in accordance with another embodiment.

FIG. 6 shows a system 600 for illuminating an object for the purpose of approximating a diffusion profile, in accordance with another embodiment. In one embodiment, such system 600 may be subject to the technique described in conjunction with FIG. 5, and/or any of the remaining figures. Of course, such system 600 may be employed in the context of any environment.

As shown, a light source 602 is used to illuminate an object 604. Further included is an occluder 606 that is situated between the source 602 and the object 604 for casting a shadow on the object 604, thus providing an occluded portion 606 and an illuminated portion 608 with an edge 607 therebetween. In other embodiments, the occluder 606 may actually touch the object 604, thus resulting in a shadow that may be perfectly sharp (assuming a perfectly sharp edge). In use, the illuminated portion 608 of the object 604 next to the occluder 606 may contain half of the shadow falloff which may be enough to analyze the diffusion profile.

In various embodiments, the object 604 may include a white diffuse object in the form of a white piece of chalk, white paper, and/or even a near-Lambertian reflector. Of course, other embodiments are contemplated where the object is grey or any other color, for that matter. Further, the object 604 may be small and placed flat against a measured surface. In particular, the object 604 may be placed to cross the shadow edge (but somewhere different from a region where diffusion is analyzed) so as to give as an accurate read of a softness of the resultant shadow, while leaving a large enough area containing the shadow edge for analysis.

As mentioned earlier, the pattern of light resulting from the occluder 606 may vary as a function of time. For example, in such embodiments, the object may be illuminated with structured light (e.g. black-white patterns such as checkerboards, barcodes, etc.) that change over time. This, in turn, allows one to estimate spatially varying diffusion across a surface of the object 604. This may be particularly useful for human faces and skin. In one optional embodiment, the foregoing pattern of light may be provided using a digital light processing (DLP) projector, a custom light emitting diode (LED)-based illuminant, a synchronized camera, eta., thus providing a rapid capture in the order of milliseconds.

In one embodiment, patterns of colored illumination may be used rather than white light, enabling a more accurate analyses of the diffusion profiles at different colors/frequency bands. For example, one can project red, green, blue, etc. light and then capture all wavelengths with a "black-and-white" camera. A rainbow may even be projected (e.g. by passing a beam of white light through a prism, etc.), and simultaneously capture all wavelengths across a visible spectrum (and into IR/UV), with an accuracy only limited by the spatial resolution of the camera. In one possible embodiment, the rainbow may run vertically, so the top scan line of camera pixels on the illuminated side may be deep red, the next scan line may be not-quite-as-deep-red, the middle scan lines may be green, the bottom scan line may be blue, etc., where each scan line may acquire a shadow integrated across a different spectral band.

In use, information may be gathered in association with one or more portions 610 (e.g. points) of the occluded portion 606 of the object 604. As shown, such information may describe light that scatters from the illuminated portion 608 of the object 604 to the occluded portion 606, and back to the illuminated portion 608, etc. Such information may, in turn, be used to approximate a diffusion profile of the object 604. More illustrative information regarding various possible techniques for approximating such diffusion profile will now be set forth in greater detail during reference to FIG. 7.

Figure 7:
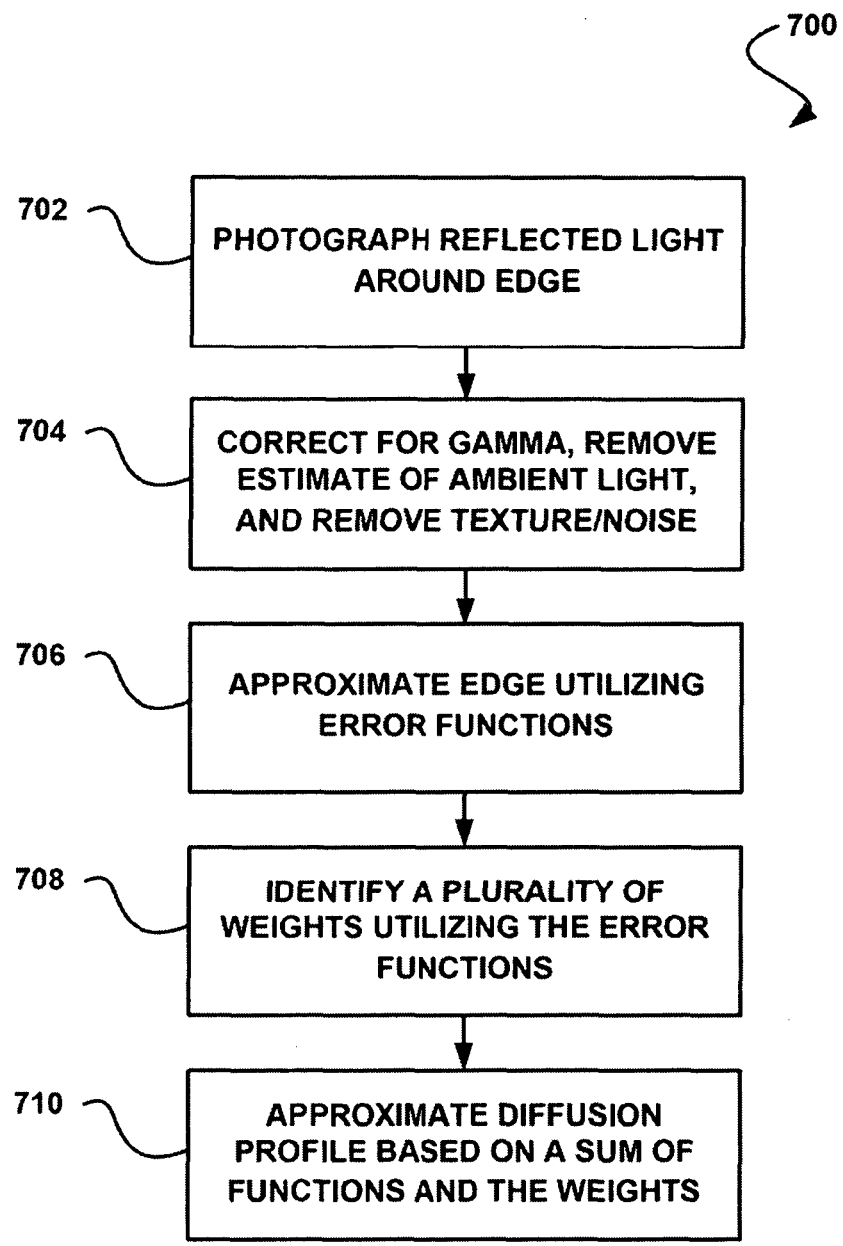
FIG. 7 shows a method for approximating a diffusion profile utilizing gathered lighting information associated with an occluded portion of an object, in accordance with another embodiment.

FIG. 7 shows a method 700 for approximating a diffusion profile utilizing gathered lighting information associated with an occluded portion of an object, in accordance with another embodiment. In one embodiment, such method 700 may be implemented in the context of the embodiments described during reference to FIGS. 5-6. Of course, such method 700 may be implemented in the context of any environment.

In operation 702, reflected light around an edge between illuminated/occluded portions of an object is photographed to produce a single image. Of course, multiple images in the form of video or the like may be provided in other embodiments, etc. In one embodiment, such photograph may be captured utilizing a low-cost camera (e.g. digital camera with less than 10, 5, 2 MPixel resolution, etc.). Of course, use of high-cost cameras is also contemplated.

Next, in operation 704, a gamma correction operation is performed if necessary, and an estimate of ambient lighting is removed. Still yet, a directional blur tangential is applied to the shadow to remove noise and texture. Such gamma correction compensates for issues that may result from a camera used for the original capture. Further, the other operations may further enhance a resultant image.

To this end, a falloff across the edge between the illuminated/occluded portions of the object (where the falloff is perpendicular to the shadow boundary) may be approximated utilizing a plurality of error functions (e.g. ERFs, etc.). See operation 706. To accomplish this, a step function that represents the transition between one side of the edge to the other may be convolved with one or more other functions. In one embodiment, such other function may take the form of a Gaussian function. Of course, use of other functions is contemplated. To this end, a resulting shadow boundary may be linearly fit with a set of error functions.

In other embodiments, error functions may not necessarily be used. For example, where the shadow is not perfect and a white or grey diffuser is used to capture the non-perfect shadow, convolving the captured shadow by Gaussians will not necessarily. result in an error function. Further, if a basis of functions other than Gaussians is used to approximate a convolution kernel or diffusion profile (even with a perfect shadow), the resulting shadow falloffs will not necessarily include error functions.

Next, in operation 708, a plurality of weights is identified utilizing the error functions. For example, a plurality of error functions may be calculated for a plurality of data points that are linearly arranged and cross the aforementioned edge. A coefficient of each of such error functions may serve as the above weights.

To this end, the diffusion profile of the object may be approximated based on a sum of functions and the weights. See operation 710. Expression #14 shows one example of how a diffusion profile $R(r)$ may be approximated utilizing Gaussian functions $G$ and weights $\omega_i$. It should be noted, however, that use of other types of functions (other than Gaussian) is contemplated.

$$R(r) = \Sigma G(v_i, r) \cdot w_i \qquad \text{Expression \#14}$$

In various embodiments, any number of components (e.g. i=1 to N, etc.) may be summed. By way of example, in some embodiments, such number N may be a function of the object itself. For instance, in the case of human skin, N may be set to six (6). With the diffusion profile approximated, an image representative of the object may be rendered, utilizing the approximation. For example, the techniques set forth during the description of the previous figures may be used for such purpose. In some embodiments, surface markers may be used for accurate scale estimation.

To this end, an image-based technique may be used to capture approximate diffusion (e.g. reflectance, transmittance, etc.) profiles for multi-layered objects. Such diffusion profiles of real-world materials may be acquired instead of or in addition to calculating them directly from scattering properties and thicknesses of various multi-layer objects, by photographing a hard shadow being cast onto the object in question. Because the object may be somewhat translucent, the shadow may not necessarily be perfectly "hard," but will rather fall off gradually as light from the illuminated portion scatters into the occluded portion. In some optional embodiments, analyzing such falloff in separate color channels may allow one to analytically fit a diffusion profile.

Thus, by photographing the shadow cast across the object, one may estimate the total incident irradiance in the scene and compensate for the not-perfectly hard shadow that will be cast by a light source and occluder. Of course, other embodiments are contemplated where no photograph is necessary and any required information is gathered using other techniques. More particularly, by noting that convolution of a step function by a kernel, $R(r)$, contains sufficient information to compute $R(r)$, a hard shadow boundary may be the subject of analysis. Further, the resulting weights may thus be used to determine a set of Gaussians or other functions which approximate the diffusion profile which, in turn, may be used for rendering purposes.

In various embodiments, scattering coefficients of a material may be estimated by analyzing a 1-D radial profile. There are two scattering coefficients for each layer of material, namely an absorption coefficient (e.g. absorption cross-section, etc.) and a scattering coefficient (e.g. scattering cross-section, etc.). A pair of such coefficients may be determined by fitting a dipole to a linear combination of Gaussians. In the case of a thin single-layer material, such coefficients may be determined by fitting a multipole to the sum of Gaussians (which estimates the original 1D profile/convolution-function used to convolve the shadow). If a multi-layer material is assumed and a convolution of dipoles and multipoles is fit to the measured 1D convolution function (approximated by a sum of Gaussians), a pair of absorption and scattering coefficients may be computed for each layer in the material. To this end, a single pair or plurality of pairs of absorption and scattering coefficients may be determined by fitting a dipole, multipole, convolutions of multipoles and dipoles are fit, etc.

In some embodiments, the foregoing technique may be used to avoid use of more expensive laser-based systems. However, additional embodiments are contemplated where the present techniques are used in combination with such laser-centric techniques. For example, such combination may be beneficial since the laser may capture local fall off more accurately, while possibly avoiding multi-exposure HDR for broad scattering, since the present techniques may potentially obtain such quite accurately. Of course, the use of such laser is set forth for illustrative purposes only, since any beam of light may be used including, but not limited to a laser beam, a focused halogen beam, a projector beam originating from a single pixel of light, and/or any other beam of light, for that matter.

To this end, a diffusion profile may be estimated within a material by analyzing both a shadow edge and a laser falloff. Error functions may be fit to the shadow edge falloff while corresponding Gaussians may be simultaneously fit to a laser profile (which may enable a more accurate profile estimate). Further, scattering coefficient estimates may also be more accurate.

Various optional applications of the foregoing technique have been contemplated. For example, where the object includes human skin, the diffusion profile of the human skin may be utilized for generating an avatar. Using the present capture technology, one may rapidly create accurate models of the scattering properties of human skin, including spatially-varying effects such as scars, freckles, vitiligo, makeup, etc. This may then be used for creating realistic avatars in a game or virtual environment, or capturing the appearance of actors in a film for special effects purposes.

In another embodiment, the diffusion profile of the human skin may be utilized for performing a medical operation and/or a cosmetic operation on the human skin. For instance, the ability to capture and analyze the light-scattering properties of human faces and skin may be applicable in the field of dermatology, since the appearance of cancerous and/or pre-cancerous lesions may be sometimes be typified by their translucence. Still yet, rashes and other skin conditions such as vitiligo may be amenable to analysis and detection as well. The ability to acquire and realistically render skin may also be useful for visualizing post-operative results (e.g. for tattoo- or varicose vein-removal procedures, etc.). In such medical applications, one may analyze the shadow fall off in more spectral channels than a typical red-green-blue camera affords, including infrared and ultraviolet wavelengths, etc.

In embodiments related to cosmetics, a tool may be used to scan exact material properties of a human face. Thereafter, realistic interactive rendering of the face may be performed under different lighting conditions and with additional layers of opaque and/or translucent materials (e.g. makeup, etc.) applied. Of course, the foregoing applications are set forth for illustrative purposes only and should not be construed as limiting in any manner whatsoever. For example, applications may range from fruit scanning, to artwork authentication, and so on.

In yet another embodiment, the environment light may be importance-sampled with a few point lights. Still yet, in still another embodiment, where minimal precomputation is available, precomputed radiance transfer (PRT) techniques may be employed to directly model single scattering. More information regarding such technique may be found with reference to WANG, R., IRAN, J., AND LUEBKE, D. 2005. All-frequency interactive relighting of translucent objects with single and multiple scattering. ACM Trans. Gr. 24, 3, 1202-1207, which is incorporated herein by reference in its entirety.

In still another embodiment, a texture chart approach may be used to correct for stretch and curvature, for example, where models with complex topology or extreme curvature exist, or where parameterized models are burdensome.

In another embodiment, the efficient analytical fitting of Gaussians may be implemented directly in the fragment shader, thus fitting profiles at every pixel every frame. This may allow support for spatially varying (i.e. texture-controlled) diffusion profiles, and building of an efficient and intuitive material editing framework for multi-layer materials.

Additionally, in another embodiment, real-time fitting to a spectral skin model may be implemented. More information regarding such model may be found with reference to "A Spectral BSSRDF for Shading Human Skin" by Craig Donner and Henrik Wann Jensen. Eurographics Symposium on Rendering (2006), which is incorporated herein by reference in its entirety.

Figure 8:
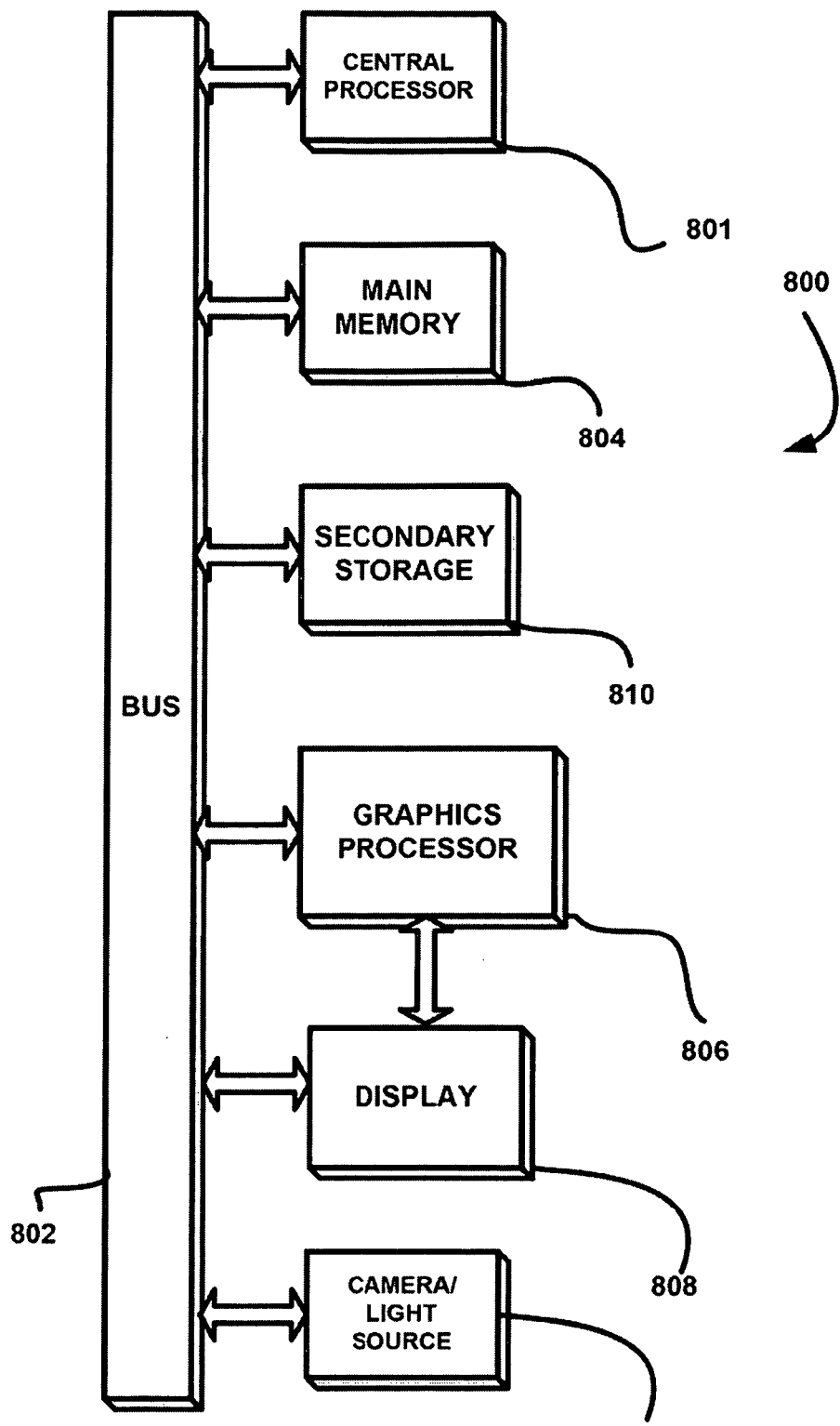
FIG. 8 illustrates an exemplary system in which the architecture and/or functionality of the various previous embodiments may be implemented.

FIG. 8 illustrates an exemplary system 800 in which the architecture and/or functionality of the various previous embodiments may be implemented. As shown, a system 800 is provided including at least one host processor 801 which is connected to a communication bus 802. The system 800 also includes a main memory 804. Control logic (software) and data are stored in the main memory 804 which may take the form of random access memory (RAM).

The system 800 also includes a graphics processor 806 and a display 808, i.e. a computer monitor. In one embodiment, the graphics processor 806 may include a plurality of shader modules, a rasterization module, etc. Each of the foregoing modules may even be situated on a single semiconductor platform to form a graphics processing unit (GPU).

In the present description, a single semiconductor platform may refer to a sole unitary semiconductor-based integrated circuit or chip. It should be noted that the term single semiconductor platform may also refer to multi-chip modules with increased connectivity which simulate on-chip operation, and make substantial improvements over utilizing a conventional central processing unit (CPU) and bus implementation. Of course, the various modules may also be situated separately or in various combinations of semiconductor platforms per the desires of the user.

The system 800 may also include a secondary storage 810. The secondary storage 810 includes, for example, a hard disk drive and/or a removable storage drive, representing a floppy disk drive, a magnetic tape drive, a compact disk drive, etc. The removable storage drive reads from and/or writes to a removable storage unit in a well known manner.

Computer programs, or computer control logic algorithms, may be stored in the main memory 804 and/or the secondary storage 810. Such computer programs, when executed, enable the system 800 to perform various functions. Memory 804, storage 810 and/or any other storage are possible examples of computer-readable media.

As an option, the system 800 may further include a camera and/or light source 812 interconnected in the manner shown. Of course, such camera and/or light source may each be packaged separately or integrated with respect to any one or more of the remaining components of the system 800. In use, such the light source may be employed to illuminate an object, while the camera may be used to capture light reflected by the object, along with information regarding a shadow resulting from any intermediate occluder, etc., for the reasons set forth during the description of previous FIGS. 5-7, for example.

In one embodiment, the architecture and/or functionality of the various previous figures may be implemented in the context of the host processor 801, graphics processor 806, an integrated circuit (not shown) that is capable of at least a portion of the capabilities of both the host processor 801 and the graphics processor 806, a chipset (i.e. a group of integrated circuits designed to work and sold as a unit for performing related functions, etc.), and/or any other integrated circuit for that matter.

Still yet, the architecture and/or functionality of the various previous figures may be implemented in the context of a general computer system, a circuit board system, a game console system dedicated for entertainment purposes, an application-specific system, and/or any other desired system. For example, the system 800 may take the form of a desktop computer, lap-top computer, and/or any other type of logic. Still yet, the system 800 may take the form of various other devices m including, but not limited to a personal digital assistant (PDA) device, a mobile phone device, a television, etc. Further, while not shown, the system 800 may be coupled to a network [e.g. a telecommunications network, local area network (LAN), wireless network, wide area network (WAN) such as the Internet, peer-to-peer network, cable network, etc.) for communication purposes.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method, comprising:
   gathering information associated with an occluded portion of a physically tangible object that is illuminated with a two-dimensional pattern of light including an edge which defines an illuminated portion and the occluded portion of the physically tangible object, the information describing light scattered from the illuminated portion of the physically tangible object and the two-dimensional pattern being provided utilizing an occluder separate from the physically tangible object that is closer to the physically tangible object than a source of the light; and approximating a diffusion profile of the physically tangible object utilizing the information;

wherein the approximating is performed utilizing a processor;

wherein prior to the approximation of the diffusion profile, a gamma correction operation is performed on the gathered information, an estimate of ambient lighting is removed from the gathered information, and noise and texture of the edge is removed from the gathered information utilizing a directional blur tangential applied to the edge.

2. The method of claim 1, wherein the physically tangible object includes a plurality of layers.

3. The method of claim 1, wherein the occluder includes a white diffuse object separate from the physically tangible object.

4. The method of claim 1, wherein the two-dimensional pattern changes as a function of time.

5. The method of claim 1, wherein the edge includes a linear edge.

6. The method of claim 1, wherein the information is gathered utilizing a camera.

7. The method of claim 1, wherein the information describes light scattered from the occluded portion.

8. A method, comprising:

gathering information associated with anon-illuminated first portion of a physically tangible object that is illuminated with a two-dimensional pattern of light including an edge which defines an illuminated second portion and the non-illuminated first portion of the physically tangible object, the information describing light scattered from the illuminated second portion of the physically tangible object; and approximating a diffusion profile of the physically tangible object, utilizing the information;

wherein the diffusion profile is approximated utilizing a plurality of Gaussian functions;

wherein the approximating is performed utilizing a processor;

wherein convolutions of multiples and dipoles are fit to the diffusion profile;

wherein the convolutions of multipoles are computed utilizing a plurality of Gaussian functions.

9. The method of claim 8, wherein a plurality of scattering coefficients is identified based an analysis involving the diffusion profile.

10. A computer program product embodied on a non-transitory computer readable medium, comprising:

computer code for gathering information associated with an occluded portion of a physically tangible object that is illuminated with a two-dimensional pattern of light including an edge which defines an illuminated portion and the occluded portion of the physically tangible object, the information describing light scattered from the illuminated portion of the physically tangible object and the two-dimensional pattern being provided utilizing an occluder separate from the physically tangible object that is closer to the physically tangible object than a source of the light; and computer code for approximating a diffusion profile of the physically tangible object utilizing the information;

wherein the computer program product is operable such that prior to the approximation of the diffusion profile, a gamma correction operation is performed on the gathered information, an estimate of ambient lighting is removed from the gathered information, and noise and texture of the edge is removed from the gathered information utilizing a directional blur tangential applied to the edge.

11. A system, comprising:

a processor for gathering information associated with an occluded portion of a physically tangible object that is illuminated with a two-dimensional pattern of light including an edge which defines an illuminated portion and the occluded portion of the physically tangible object, and approximating a diffusion profile of the physically tangible object utilizing the information, the information describing light scattered from the illuminated portion of the physically tangible object and the two-dimensional pattern being provided utilizing an occluder separate from the physically tangible object that is closer to the physically tangible object than a source of the light;

wherein the system is operable such that prior to the approximation of the diffusion profile, a gamma correction operation is performed on the gathered information, an estimate of ambient lighting is removed from the gathered information, and noise and texture of the edge is removed from the gathered information utilizing a directional blur tangential applied to the edge.

12. The system of claim 11, wherein the processor remains in communication with a sensor for sensing the light, and the light source for illuminating the object.

13. The method of claim 1, wherein the two-dimensional pattern of light includes a structured light that changes over time.

14. The method of claim 1, wherein the two-dimensional pattern of light is provided using a custom light emitting diode (LED)-based illuminant.

15. The method of claim 1, wherein the two-dimensional pattern of light is provided using a digital light processing (DLP) projector.

16. The method of claim 1, wherein the information describes the light scattered from the illuminated portion of the physically tangible object to the occluded portion of the physically tangible object and back to the illuminated portion of the physically tangible object.

17. A computer program product embodied on a non-transitory computer readable medium, comprising:

computer code for gathering information associated with a non-illuminated first portion of a physically tangible object that is illuminated with a two-dimensional pattern of light including an edge which defines an illuminated second portion and the non-illuminated first portion of the physically tangible object, the information describing light scattered from the illuminated second portion of the physically tangible object; and computer code for approximating a diffusion profile of the physically tangible object, utilizing the information;

wherein the computer program product is operable such that the diffusion profile is approximated utilizing a plurality of Gaussian functions;

wherein the computer program product is operable such that convolutions of multipoles and dipoles are fit to the diffusion profile;

wherein the computer program product is operable such that the convolutions of multipoles are computed utilizing a plurality of Gaussian functions.

18. A system, comprising:

a processor for gathering information associated with a non-illuminated first portion of a physically tangible object that is illuminated with a two-dimensional pattern of light including an edge which defines an illuminated second portion and the non-illuminated first portion of the physically tangible object, and approximating a diffusion profile of the physically tangible object, utilizing the information, the information describing light scattered from the illuminated second portion of the physically tangible object;

wherein the diffusion profile is approximated utilizing a plurality of Gaussian functions;

wherein the system is operable such that convolutions of multipoles and dipoles are fit to the diffusion profile;

wherein the system is operable such that the convolutions of multipoles are computed utilizing a plurality of Gaussian functions.

* * * * *